(12) United States Patent
Norton et al.

(10) Patent No.: US 10,472,984 B2
(45) Date of Patent: *Nov. 12, 2019

(54) APPARATUS FOR INSERTION INTO A CAVITY OF AN OBJECT

(71) Applicant: ROLLS-ROYCE PLC, London (GB)

(72) Inventors: Andrew D Norton, Derby (GB); Amir Rabani, Nottingham (GB); States Chiwanga, Newmarket (GB)

(73) Assignee: ROLLS-ROYCE plc, London (GB)

( * ) Notice: Subject to any disclaimer, the term of this patent is extended or adjusted under 35 U.S.C. 154(b) by 197 days.

This patent is subject to a terminal disclaimer.

(21) Appl. No.: 15/680,619

(22) Filed: Aug. 18, 2017

(65) Prior Publication Data

US 2018/0163561 A1 Jun. 14, 2018

(30) Foreign Application Priority Data

Sep. 12, 2016 (GB) .................................. 1615429.6

(51) Int. Cl.
| | | |
|---|---|---|
| *F28D 15/04* | (2006.01) | |
| *F01D 21/00* | (2006.01) | |
| *G01N 21/954* | (2006.01) | |
| *G01M 15/14* | (2006.01) | |

(52) U.S. Cl.
CPC ........... *F01D 21/003* (2013.01); *F28D 15/04* (2013.01); *G01N 21/954* (2013.01); *F05D 2230/80* (2013.01); *F05D 2260/83* (2013.01); *G01M 15/14* (2013.01); *G01N 2021/9542* (2013.01)

(58) Field of Classification Search
None
See application file for complete search history.

(56) References Cited

U.S. PATENT DOCUMENTS

| 4,108,239 | A | * | 8/1978 | Fries ....................... B22F 7/002 |
| | | | | 165/104.26 |
| 4,419,044 | A | | 12/1983 | Barry et al. |
| 4,461,343 | A | * | 7/1984 | Token ................. F28D 15/0233 |
| | | | | 165/104.26 |
| 4,643,022 | A | | 2/1987 | Werlberger et al. |

(Continued)

FOREIGN PATENT DOCUMENTS

| EP | 1942249 A2 | 7/2008 |
| GB | 2090333 A | 7/1982 |
| WO | 2013/116475 A1 | 8/2013 |

OTHER PUBLICATIONS

Jan. 12, 2018 Search Report issued in European Patent Application No. 17186862.

(Continued)

*Primary Examiner* — Michael Lebentritt
(74) *Attorney, Agent, or Firm* — Oliff PLC

(57) ABSTRACT

Apparatus for insertion into a cavity of an object, the apparatus comprising: a first tube comprising a first end, a second end and a first cavity extending between the first end and the second; a member positioned within the first cavity of the first tube and configured to enable an action to be performed; a heat pipe including a first end, a second end, and a second cavity extending between the first end and the second end, the first tube being positioned within the second cavity of the heat pipe; and an actuator configured to move the first tube relative to the heat pipe.

20 Claims, 8 Drawing Sheets

(56) References Cited

U.S. PATENT DOCUMENTS

| | | | |
|---|---|---|---|
| 5,979,220 A | 11/1999 | Zombo et al. | |
| 6,080,962 A | 6/2000 | Lee | |
| 6,091,489 A * | 7/2000 | Welker | G02B 23/2407 356/241.1 |
| 6,233,937 B1 * | 5/2001 | Gray | F01K 13/025 415/116 |
| 6,364,003 B1 | 4/2002 | Liu et al. | |
| 6,749,395 B1 * | 6/2004 | Reichert | F01D 17/14 415/115 |
| 7,900,438 B2 | 3/2011 | Venkataramani et al. | |
| 8,015,788 B2 * | 9/2011 | Stephenson | F01D 5/046 415/114 |
| 8,353,334 B2 | 1/2013 | Zhao et al. | |
| 8,397,516 B2 * | 3/2013 | Maldonado | F01D 9/041 415/115 |
| 9,797,310 B2 * | 10/2017 | Ekanayake | F01K 23/02 |
| 9,909,448 B2 * | 3/2018 | Gerstler | F01D 9/041 |
| 2006/0006339 A1 | 1/2006 | Fraser et al. | |
| 2007/0084587 A1 * | 4/2007 | Huang | B22F 5/106 165/104.26 |
| 2007/0199384 A1 | 8/2007 | Kuznar | |
| 2007/0240854 A1 * | 10/2007 | Liu | F28D 15/046 165/104.26 |
| 2007/0277963 A1 * | 12/2007 | Hou | F28D 15/046 165/104.26 |
| 2009/0076332 A1 * | 3/2009 | Iwasaki | A61B 1/00096 600/168 |
| 2012/0227925 A1 * | 9/2012 | Sweeney | F01K 3/186 165/10 |
| 2013/0126139 A1 * | 5/2013 | Tsuruta | F28D 15/0233 165/170 |
| 2013/0168052 A1 * | 7/2013 | Meyer, IV | B32B 5/16 165/104.26 |
| 2013/0330168 A1 * | 12/2013 | Liotta | F01D 17/085 415/1 |
| 2014/0034848 A1 * | 2/2014 | Campbell | F03G 6/00 250/492.1 |
| 2014/0063227 A1 * | 3/2014 | Baleine | G02B 23/2492 348/82 |
| 2015/0300260 A1 * | 10/2015 | Wollenweber | F23K 5/005 60/39.12 |
| 2017/0314871 A1 * | 11/2017 | Basu | H01L 21/4871 |
| 2018/0058233 A1 * | 3/2018 | Norton | F01D 11/003 |

OTHER PUBLICATIONS

Feb. 14, 2017 Search Report issued in British Patent Application No. 1615429.6.

A.L. Phillips et al. "Loop Heat Pipe Qualification for High Vibration and High-G Environments". American Institute of Aeronautics and Astronautics, 1997, pp. 1-6.

* cited by examiner

APPARATUS FOR INSERTION INTO A CAVITY OF AN OBJECT

TECHNOLOGICAL FIELD

The present disclosure concerns apparatus for insertion into a cavity of an object.

BACKGROUND

Gas turbine engines may sustain wear and/or damage during operation that may reduce the efficiency of the gas turbine engine. Inspection and repair of a gas turbine engine may be a relatively time consuming task and may require disassembly of the gas turbine engine. For example, gas turbine engines used in aviation are usually mounted on a wing of an aircraft. Inspection and repair of such a gas turbine engine may require the gas turbine engine to be removed from the wing of the aircraft and then disassembled to allow access to the worn and/or damaged component.

BRIEF SUMMARY

According to various examples there is provided apparatus for insertion into a cavity of an object, the apparatus comprising: a first tube comprising a first end, a second end and a first cavity extending between the first end and the second; a member positioned within the first cavity of the first tube and configured to enable an action to be performed; a heat pipe including a first end, a second end, and a second cavity extending between the first end and the second end, the first tube being positioned within the second cavity of the heat pipe; and an actuator configured to move the first tube relative to the heat pipe.

The heat pipe may comprise a first part extending along a first longitudinal axis and including the second cavity, and a second part extending along a second longitudinal axis, the second longitudinal axis defining an angle with the first longitudinal axis.

The second longitudinal axis may define an angle of ninety degrees with the first longitudinal axis.

The heat pipe may include: an inner region for enabling fluid to flow to the second end of the heat pipe; an outer region for enabling fluid to flow to the second end of the heat pipe; and a channel for enabling vapour to flow to the first end of the heat pipe.

The inner region may comprise a lattice structure defining a plurality of pores.

The outer region may comprise a lattice structure defining a plurality of pores.

The plurality of pores may have a median dimension in the range of five micrometres to two hundred and fifty micrometres.

The plurality of pores may have a median dimension in the range of thirty micrometres to one hundred and twenty micrometres.

The inner region may comprise a plurality of grooves and the outer region may comprise a plurality of grooves.

The channel may comprise a plurality of conduits that are interconnected at the first end of the heat pipe.

The apparatus may further comprise a plug coupled to the second end of the first tube. The actuator may be configured to move the first tube between a first position in which the plug seals the member from the cavity of the object, and a second position in which the member is exposed to the cavity of the object.

The apparatus may further comprise a connector arrangement configured to connect the apparatus to the object.

The connector arrangement may be configured to enable an operator to connect the apparatus to the object, and to enable the operator to disconnect and remove the apparatus from the object.

The member may comprise one or more optical fibres. The apparatus may further comprise an optical sensor coupled to the one or more optical fibres.

The optical sensor may be positioned external to the first tube.

The member may comprise an optical sensor.

The member may comprise repair apparatus for performing a repair on the object.

The member may comprise non-destructive examination (NDE) apparatus.

The object may be a gas turbine engine.

The cavity may be a gas path of the gas turbine engine.

According to various examples there is provided apparatus for insertion into a cavity of an object, the apparatus comprising: a first tube comprising a first end and a second end; a member coupled to the first tube and configured to enable an action to be performed; a heat pipe including a first end, a second end, and a second cavity extending between the first end and the second end, the first tube being positioned within the second cavity of the heat pipe; and an actuator configured to move the first tube relative to the heat pipe.

According to various examples there is provided a system comprising: a gas turbine engine including a first inspection port; and an apparatus as described in any of the preceding paragraphs extending inside the first inspection port.

The gas turbine engine may further comprise a second inspection port, and the system may further comprise another apparatus as described in any of the preceding paragraphs extending inside the second inspection port.

The first end of the heat pipe may be positioned within a bypass duct of the gas turbine engine.

The skilled person will appreciate that except where mutually exclusive, a feature described in relation to any one of the above aspects may be applied mutatis mutandis to any other aspect. Furthermore except where mutually exclusive any feature described herein may be applied to any aspect and/or combined with any other feature described herein.

BRIEF DESCRIPTION

Embodiments will now be described by way of example only, with reference to the Figures, in which.

DETAILED DESCRIPTION

In the following description, the terms 'connected' and 'coupled' mean operationally connected and coupled. It should be appreciated that there may be any number of intervening components between the mentioned features, including no intervening components.

Figure 1:
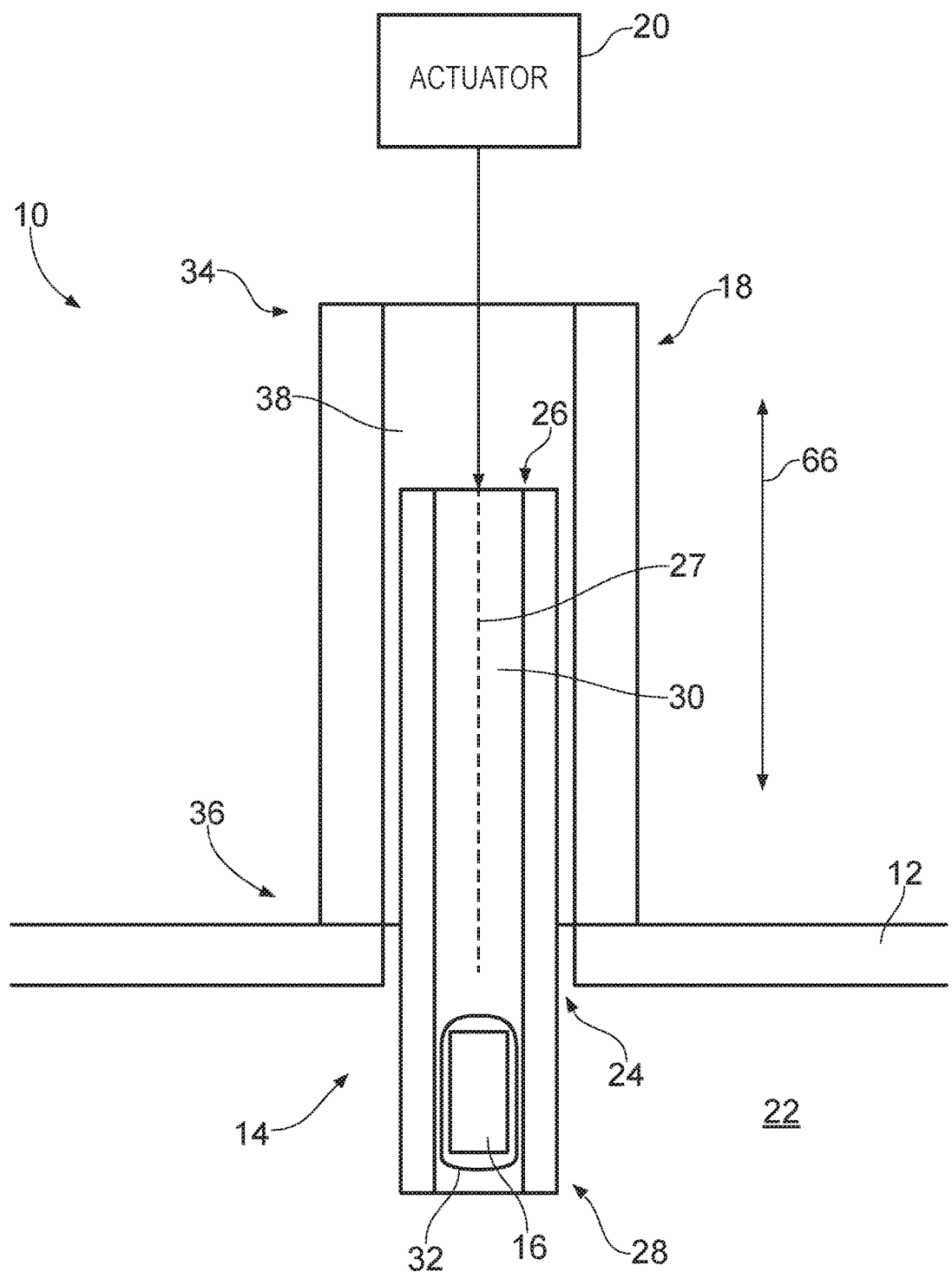
FIG. 1 illustrates a schematic cross sectional side view of apparatus for insertion into a cavity of an object according to various examples.

FIG. 1 illustrates a schematic cross sectional view of apparatus 10 and an object 12 according to various examples. The apparatus 10 includes a first tube 14, a member 16, a heat pipe 18, and an actuator 20.

The object 12 may be any article, module, component, part, or assembly of components that define a cavity 22 and an opening 24 to the cavity 22. For example, the object 12 may be a gas turbine engine or a module of a gas turbine engine. In a further example, the object 12 may be an internal combustion engine for a vehicle. Alternatively, the object 12 may be a pipeline, a storage tank, or other container. Where the object 12 is a gas turbine engine, or a module of a gas turbine engine, the opening 24 may be a borescope port and the cavity 22 may be a gas path within the gas turbine engine.

In summary, the apparatus 10 may be inserted into the cavity 22 of the object 12 via the opening 24 to enable an inspection, a repair activity, or a non-destructive examination to be performed. The heat pipe 18 is arranged to transfer thermal energy from the member 16 and may thereby prevent the member 16 from being damaged by high temperatures within the cavity 22.

The first tube 14 extends along a longitudinal axis 27 and includes a first end 26 and a second opposite end 28. The first tube 14 may have any suitable cross sectional shape and may have, for example, a circular, elliptical, or a polygonal cross sectional shape. The first tube 14 also includes a first cavity 30 that extends between the first end 26 and the second end 28 along the longitudinal axis 27. In some examples, the first cavity 30 extends from the first end 26 to the second end 28 and the first end 26 and the second end 28 may be open. In other examples, the first cavity 30 has a length along the longitudinal axis 27 that is less than the length of the first tube 14 along the longitudinal axis 27 and consequently, the first end 26 and/or the second end 28 may be closed.

The first tube 14 may also include an aperture 32 that provides an opening to the cavity 30. The aperture 32 may have any suitable shape and may be circular, elliptical or have a polygonal shape for example. The aperture 32 may be located at the second end 28 of the first tube 14 as illustrated in FIG. 1. In other examples, the aperture 32 may be located at any position between the first end 26 and the second end 28. The aperture 32 may be an open aperture or may be covered by a material that is transparent to electromagnetic waves within one or more portions of the electromagnetic spectrum. For example, the aperture 32 may be covered by glass that is transparent to light.

The member 16 may be positioned within the first cavity 30 of the first tube 14 and may be positioned adjacent the aperture 32 of the first tube 14. In some examples, the member 16 may completely cover the aperture 32 (and may or may not seal the aperture 32). In other examples, the member 16 may only partially cover the aperture 32. The member 16 is configured to enable one or more actions to be performed. The actions may include (but are not limited to) an inspection activity, and/or a repair activity, and/or a machining activity and these are described in greater detail in the following paragraphs.

The member 16 may comprise inspection apparatus for enabling the interior of the object 12 to be inspected by a human operator and/or a computer. For example, the member 16 may comprise an optical sensor (such as a charge coupled device (CCD) camera, or a complementary metal oxide semiconductor (CMOS) camera) at the second end 28 of the first tube 14 to enable electromagnetic waves to be received via the aperture 32 and/or the second end 28 (where the second end 28 is open). The member 16 may also comprise a device for emitting electromagnetic waves (such as a laser, a light emitting diode, a halogen bulb for example) positioned at the second end 28 to enable electromagnetic waves to be emitted from the aperture 32 and/or the second end 28 (where the second end 28 is open). The optical sensor and the emitter may be connected to a processor and memory positioned outside of the first cavity 30 via one or more cables.

In some examples where the member 16 comprises inspection apparatus, the member 16 may comprise one or more nozzles for injecting an inspection fluid into the cavity 22 of the object 12. For example, where the member 16 comprises an ultrasonic transducer, the member 16 may additionally comprise one or more nozzles for injecting water into the cavity 22 of the object 12.

In other examples, the member 16 may comprise one or more optical fibres to enable electromagnetic waves to be transmitted from the aperture 32 (and/or open second end 28 of the first tube 14) and/or to enable electromagnetic waves to be received via the aperture 32 (and/or open second end 28 of the first tube 14). The apparatus 10 may further comprise an optical sensor (such as a charge coupled device (CCD) camera, or a complementary metal oxide semiconductor (CMOS) camera) coupled to the one or more optical fibres. The optical sensor may be positioned external to the first tube 14 or may be positioned internal to the first tube 14 (at the first end 26 of the first tube 14 for example). The apparatus 101 may also comprise a device for emitting electromagnetic waves (such as a laser, a light emitting diode, a halogen bulb for example) that is coupled to the one or more optical fibres. The device for emitting electromagnetic waves may be positioned external to the first tube 14 or may be positioned internal to the first tube 14 (for example, at the first end 26 of the first tube 14).

Additionally or alternatively, the member 16 may comprise repair apparatus for performing a repair on the object 12. For example, the apparatus 16 may comprise one or more optical fibres and a laser as described in the preceding paragraph to enable the apparatus 10 to clean the object 12 or to drill the object 12. In another example, the member 16 may comprise one or more nozzles for spraying a coating on the object 12. In a further example, the member 16 may comprise one or more nozzles and a pump for extracting fluid from the cavity 22 of the object 12 (for example, to create a vacuum in the cavity 22). In another example, the member 16 may comprise one or more nozzles for injecting a braze into the cavity 22 of the object 12.

Additionally or alternatively, the member 16 may comprise non-destructive examination (NDE) apparatus (which may also be referred to as non-destructive testing (NDT) apparatus). For example, the member 16 may comprise one or more optical fibres, a sensor (as described above) and a computer for enabling non-destructive examination to be performed. In another example, the member 16 may comprise an ultrasonic transducer and a computer for enabling non-destructive examination to be performed. In a further example, the member 16 may comprise infrared and thermal testing apparatus for enabling non-destructive examination to be performed. It should be appreciated that the member 16 may comprise any suitable non-destructive examination apparatus and is not limited to the examples provided above.

The heat pipe 18 may be any suitable heat pipe or thermosiphon and may also be referred to as a second tube. The heat pipe 18 may be coated with any suitable material. For example, the heat pipe 18 may be coated with a nickel alloy. The heat pipe 18 includes a first end 34 and an opposite second end 36. The heat pipe 18 may have any suitable cross sectional shape (when viewed in plan) and may have a circular cross sectional shape, an elliptical cross sectional shape, or a polygonal cross sectional shape. The heat pipe 18 may be shaped and sized to not fit within the opening 24 of the object 12 and consequently, the heat pipe 18 may abut the outer surface of the object 12 (as illustrated in FIG. 1). In other examples, the heat pipe 18 may be shaped and sized to fit within the opening 24 of the object 12.

The heat pipe 18 defines a second cavity 38 that extends between the first end 34 and the second end 36 of the heat pipe 18. As illustrated in FIG. 1, the first end 34 and the second end 36 are open and the first tube 14 is positioned within the second cavity 38 of the heat pipe 18. In some examples, the first tube 14 and the heat pipe 18 are arranged concentrically and share the longitudinal axis 27. In other examples, the first tube 14 and the heat pipe 18 are not arranged concentrically and consequently have separate longitudinal axes.

Figure 2:
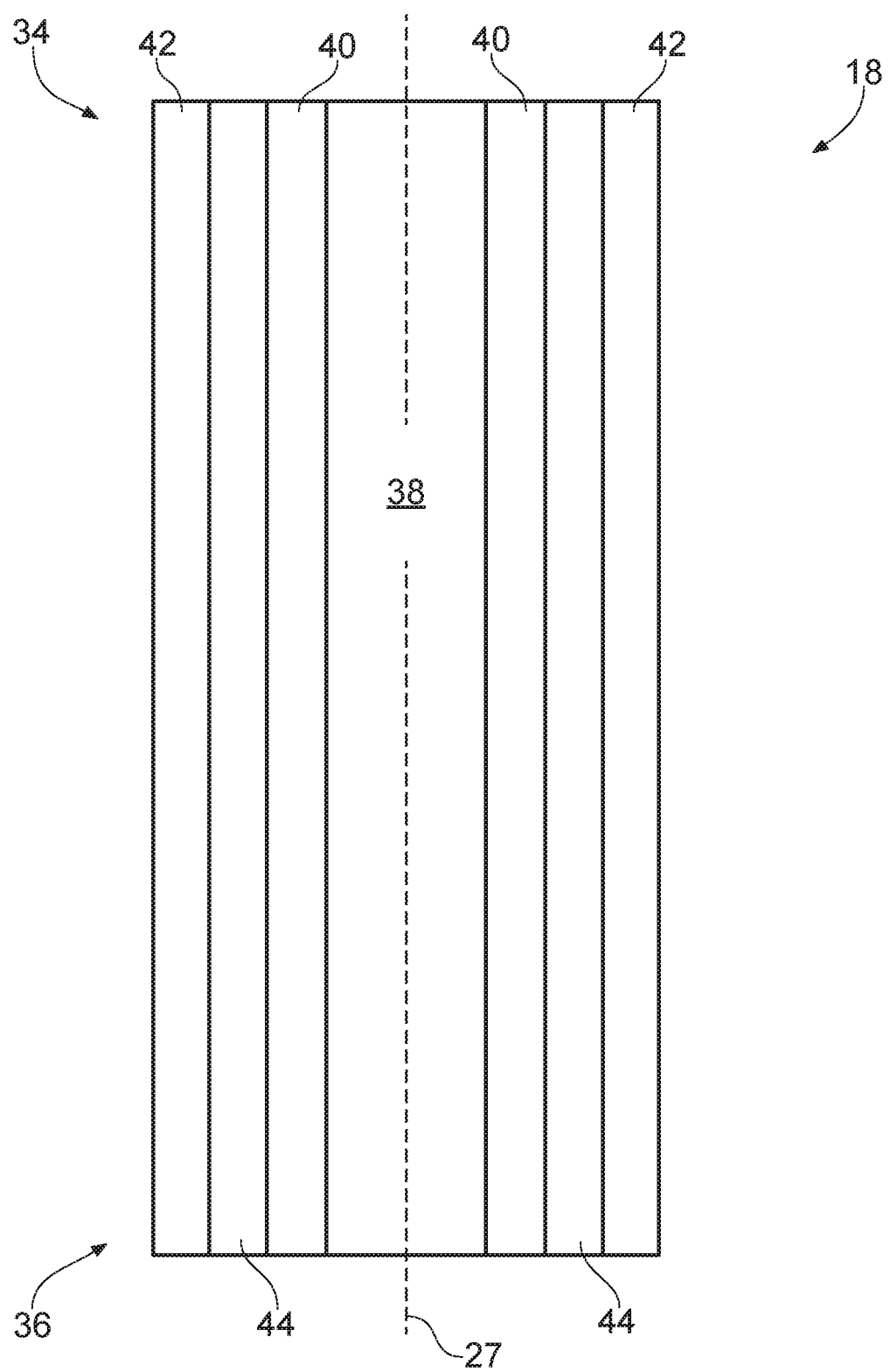
FIG. 2 illustrates a schematic cross sectional side view of a heat pipe according to various examples.

As illustrated in FIG. 2, the heat pipe 18 may include: an inner region 40; an outer region 42; a channel 44 between the inner region 40 and the outer region 42; and a fluid.

The inner region 40 and the outer region 42 may have any suitable dimensions. For example, the inner region 40 and/or the outer region 42 may have a thickness (as measured perpendicular to the longitudinal axis 27) in the range of one hundred micrometres to three thousand micrometres. In some examples, the inner region 40 and/or the outer region 42 may have a thickness in the range of three hundred micrometres to one thousand micrometres. It should be appreciated that the inner region 40 and the outer region 42 may have the same thickness, or may have different thicknesses.

The fluid may be any suitable fluid for a heat pipe. For example, the fluid may be: an alkali metal (for example, caesium, potassium, and sodium) or an alloy of alkali metal (such as NaK); an organic compound (for example, naphthalene, acetone, hydrocarbons such as ethane, alcohols such as methanol, and amines such as methylamine); a transition metal (mercury or silver for example); a post-transition metal (such as indium); water; or ammonia.

In operation, the fluid flows as a liquid between the first end 34 and the second end 36 in the inner region 40 and the outer region 42, and flows as a vapour between the first end 34 and the second end 36 in the channel 44. For example, where the second end 36 is located at a higher temperature location than the first end 34 (as illustrated in FIG. 1), the fluid flows as a liquid from the first end 34 to the second end 36 in the inner region 40 and the outer region 42, vaporises at the second end 36, flows as a vapour from the second end 36 to the first end 34 in the channel 44, and then condenses at the first end 34. It should be appreciated that the fluid may flow as a liquid in the inner region 40 and the outer region 42 via capillary action.

Figure 3:
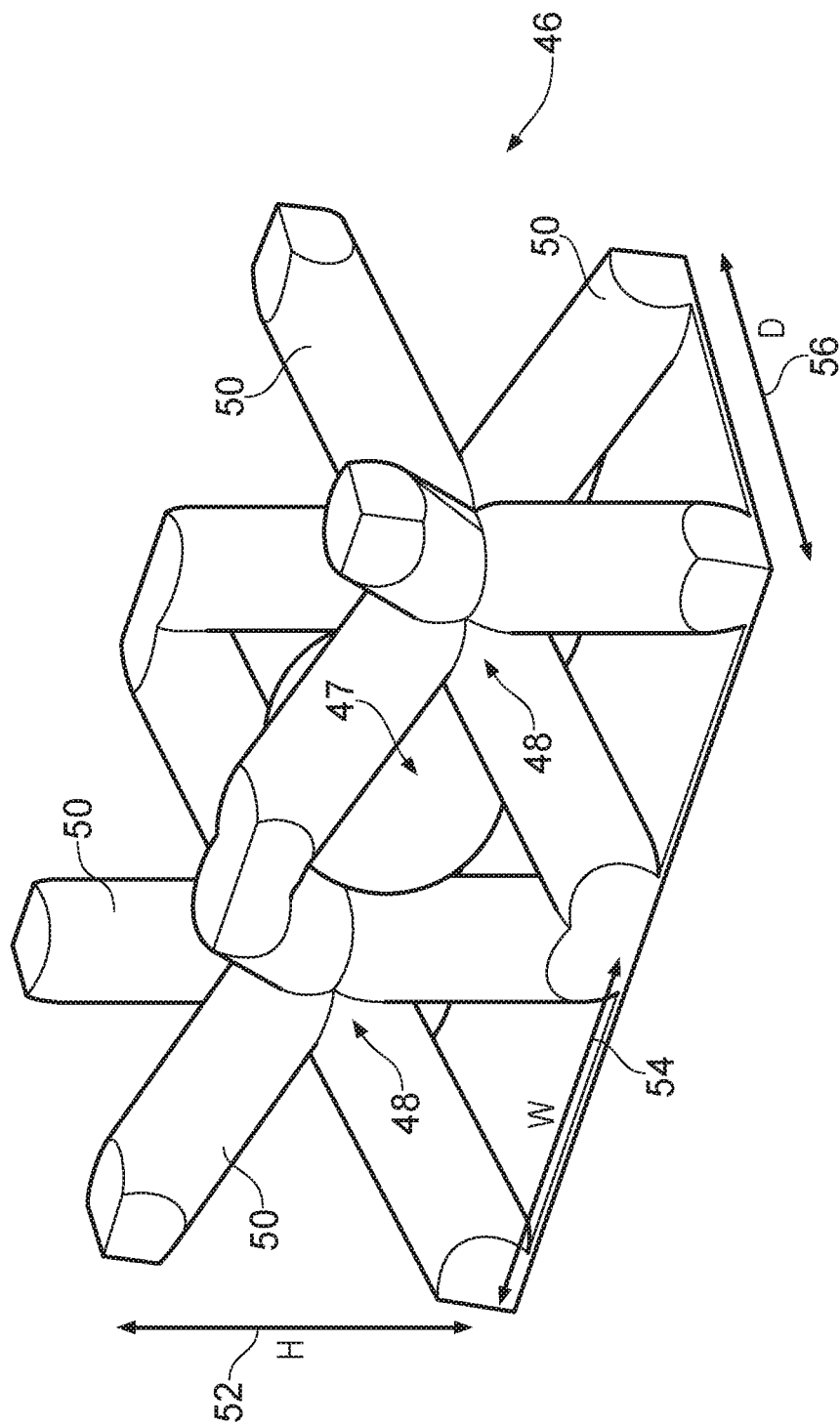
FIG. 3 illustrates a schematic perspective view of a lattice structure of a heat pipe according to various examples.

The inner region 40 and/or the outer region 42 may comprise a lattice structure 46 defining a plurality of pores 47 as illustrated in FIG. 3. The lattice structure 46 includes a plurality of nodes 48, and a plurality of links 50 that extend between the plurality of nodes 48 and define the plurality of pores 47. The lattice structure 46 may be manufactured using an additive layer manufacturing (ALM) technique such as Selective Laser Melting (SLM). Alternatively, the lattice structure 46 may be manufactured using an alternative manufacturing process. For example, the lattice structure 46 may be manufactured by wrapping a mesh multiple times around the inside of a tube. By way of another example, the lattice structure 46 may be manufactured using laser drilling. By way of a further example, the lattice structure 46 may be manufactured by poorly sintering a powder. By way of another example, the lattice structure 46 may be manufactured using a powder sintering process.

In more detail, adjacent nodes in the plurality of nodes 48 define a height (H) 52, a width (W) 54, and a depth (D) 56 and thus define the dimensions of the plurality of pores 47. The height (H) 52, the width (W) 54 and the depth (D) 56 may be the same as one another, or may be different to one another. Furthermore, the dimensions of the plurality of pores 47 may vary between different nodes 48. For example, the width (W) 54 between adjacent nodes 48 may increase or decrease between the first end 34 and the second end 36 of the heat pipe 18.

In various examples, the plurality of pores 47 have a median dimension (that is, height (H) 52, and/or width (W) 54, and/or depth (D) 56) in the range of five micrometres to two hundred and fifty micrometres and may have a median dimension in the range of thirty micrometres to one hundred and twenty micrometres. The inner region 40 and/or the outer region 42 may be relatively thin and may have a thickness in the range of five hundred micrometres to one thousand micrometres (measured perpendicularly to the longitudinal axis 27). Consequently, the inner region 40 and/or the outer region 42 may advantageously have relatively low capillary losses.

Figure 4:
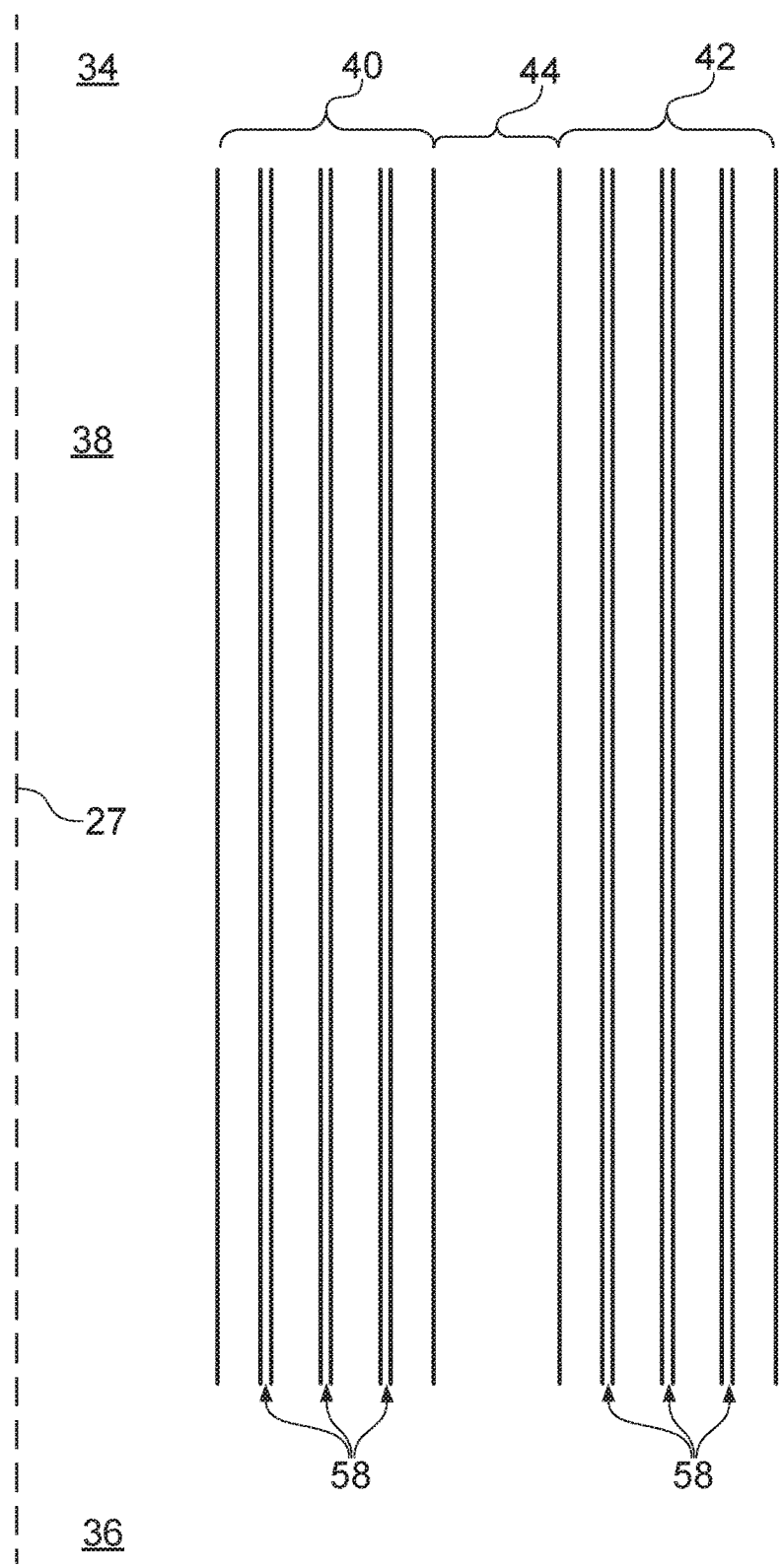
FIG. 4 illustrates a schematic cross sectional side view of a heat pipe comprising a plurality of grooves according to various examples.

In other examples, the inner region 40 and/or the outer region 42 may comprise a plurality of grooves 58 as illustrated in FIG. 4. The plurality of grooves 58 are oriented parallel to the longitudinal axis 28 and extend between the first end 34 and the second end 36 of the heat pipe 18. The plurality of grooves 58 may be formed through an additive layer manufacturing (ALM) process such as selective layer melting (SLM). The plurality of grooves 58 may be hollow, or may comprise the lattice structure 46 therein.

The grooves 58 may have a width (measured perpendicular to the longitudinal axis 27) in the range of fifty micrometres to three hundred micrometres. The gaps between adjacent grooves 58 may have a width (also measured perpendicular to the longitudinal axis 27) in the range of fifty micrometres to three hundred micrometres.

The regions adjacent to the plurality of grooves 58 within the inner region 40 and the outer region 42 may be solid, or may be porous and comprise the lattice structure described in the preceding paragraphs. The gaps between adjacent grooves 58 may be open, or may comprise a porous structure (such as the lattice structure described in the preceding paragraphs).

Figure 5:
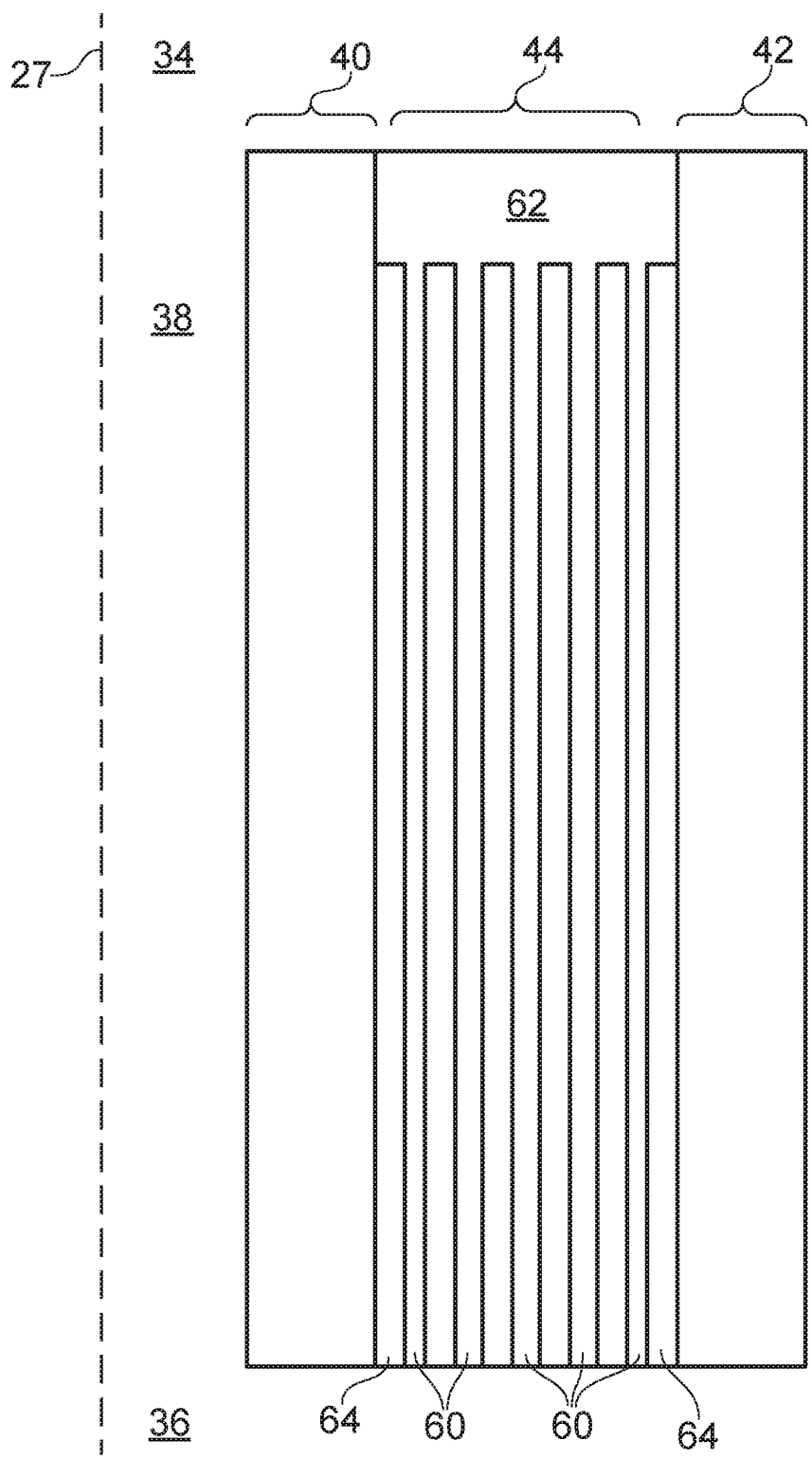
FIG. 5 illustrates a schematic cross sectional side view of a heat pipe comprising a channel defining a plurality of conduits according to various examples.

The channel 44 may comprise a plurality of conduits 60 that are interconnected at the first end 34 of the heat pipe 18 to form a chamber 62 as illustrated in FIG. 5. The plurality of conduits 60 are oriented parallel to the longitudinal axis 27 and extends between the first end 34 and the second end 36 of the heat pipe 18. The channel 44 may provide an advantage in that liquid may flow from the first end 34 to the second end 36 via the plurality of conduits 60, vaporise, and then return to the first end 34 via adjacent conduits 64 (which may comprise the lattice structure 46).

The actuator 20 may include any suitable device for moving the first tube 14 relative to the heat pipe 18. For example, the actuator 20 may include a servo-motor, a hydraulic cylinder, a pneumatic cylinder, a rack and pinion, a cam rotatable on a shaft, or a lead screw. The actuator 20 is configured to move the first tube 14 relative to the heat pipe 18 and parallel to the longitudinal axis 27 as indicated by arrow 66. The actuator 20 may be configured to move the first tube 14 between a first position in which the member 16 is located within the cavity 22 (and outside of the heat pipe 18), and a second position in which the member 16 is located within the heat pipe 18 (and may not be located within the cavity 22).

The apparatus 10 may provide several advantages. First, the apparatus 10 may enable an action (such as inspection, repair, non-destructive examination) to be performed within the cavity 22 of the object 12 when the member 16 is positioned within the cavity 22 (that is, when the first tube 14 is in the first position). Second, the heat pipe 18 may transfer thermal energy from the member 16 when the first tube 14 is in the second position. This may allow the apparatus 10 to be coupled to the object 12 when the object 12 is in operation and the cavity 22 is at a relatively high temperature. The heat pipe 18 may thus prevent the member 16 from being damaged by the relatively high temperatures in the cavity 22. In some examples, the apparatus 10 may advantageously be used when the object 12 is in operation (for example, during start-up of a gas turbine engine) and the temperature within the cavity 22 is within the operating temperature range of the member 16.

Figure 6:
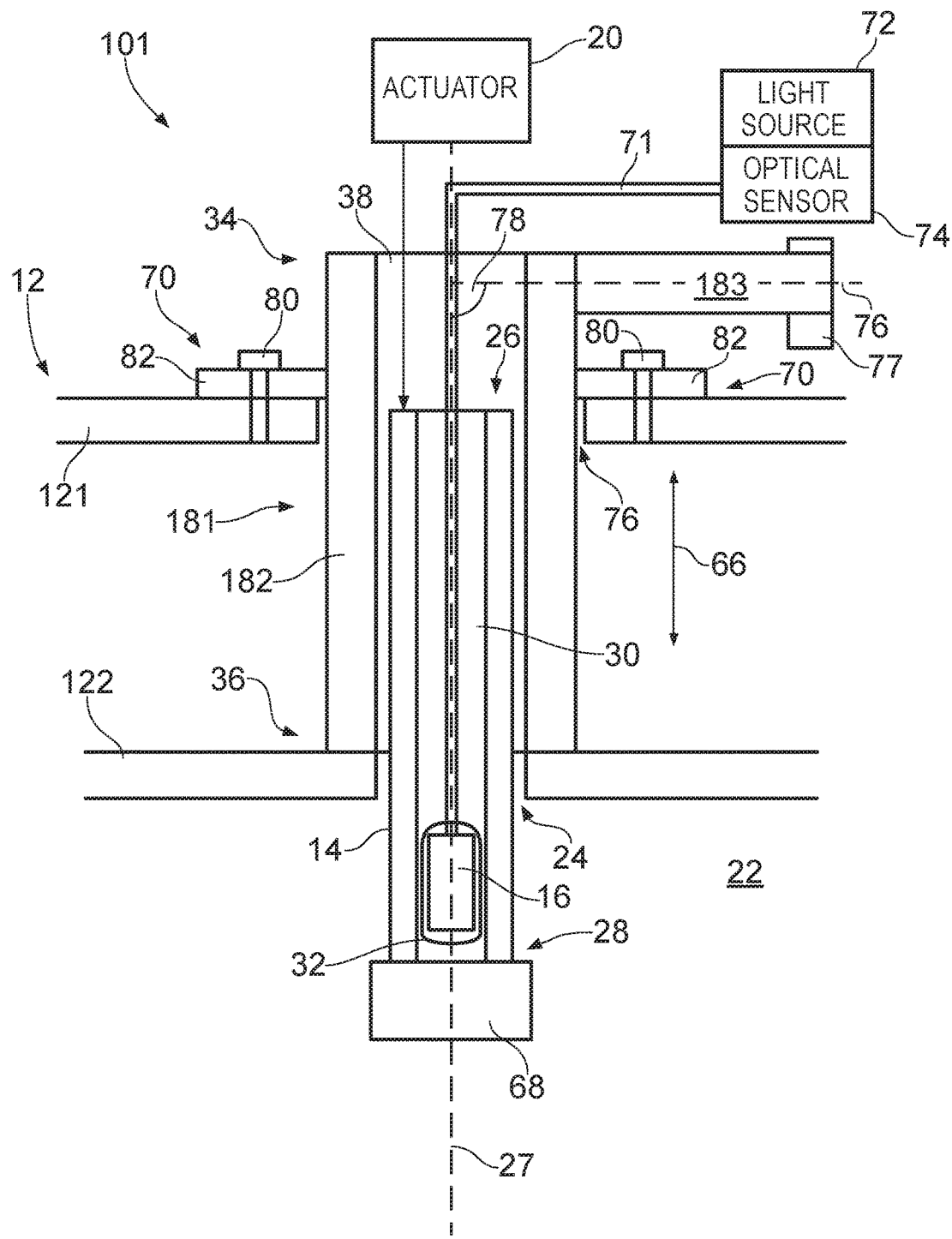
FIG. 6 illustrates a schematic cross sectional side view of another apparatus for insertion into a cavity of an object according to various examples.

FIG. 6 illustrates a schematic side view of another apparatus 101 and an object 12. The apparatus 101 is similar to the apparatus 10 illustrated in FIG. 1 and where the features are similar, the same reference numerals are used. The apparatus 101 differs from the apparatus 10 in that the apparatus 101 further comprises a heat pipe 181, a plug 68, a connector arrangement 70, one or more optical fibres 71, a light source 72, and an optical sensor 74.

The heat pipe 181 differs from the heat pipe 18 illustrated in FIG. 1 in that the heat pipe 181 comprises a first part 182 extending along the longitudinal axis 27 and includes the second cavity 38, and also a second part 183 extending along a second longitudinal axis 76. The second longitudinal axis 76 defines an angle 78 with the first longitudinal axis 27. In some examples, the second longitudinal axis 76 defines an angle 78 of ninety degrees with the first longitudinal axis 27. In other examples, the angle 78 may be any acute angle or any obtuse angle. Furthermore, the first part 181 and/or the second part 182 may be curved along at least a portion of their lengths in other examples.

The second part 183 of the heat pipe 181 may extend from the first end 34 of the first part 182 of the heat pipe 181 as illustrated in FIG. 6. In other examples, the second part 183 of the heat pipe 181 may extend from first part 182 of the heat pipe 181 at any location between the first end 34 and the second end 36.

The second part 183 may have the same structure, or a different structure to the first part 182. Therefore, the second part 183 may have an internal structure as illustrated in any of FIGS. 2, 3, 4, and 5. For example, the second part 183 may include a channel surrounded by porous regions (as illustrated in FIG. 3) or grooved regions (as illustrated in FIG. 4). The channel may be hollow or may have the structure illustrated in FIG. 5 (that is, the channel may comprise a plurality of conduits interconnected by a chamber). The channel of the second part 183 is connected to the channel 44 of the first part 182, and the porous regions/grooved regions of the second part 183 are connected to the inner and outer regions 40, 42 of the first part 182. Where the first part 182 and the second 183 comprise grooved regions, it should be appreciated that the grooved regions are connected to one another to permit move of fluid between the first part 182 and the second part 183.

The second part 183 may comprise a device 77 for increasing the transfer of thermal energy from the second part 183. For example, the device may comprise a heat sink 77 that increases the transfer of thermal energy from the second part 183. The heat sink 77 may be positioned at the free end of the second part 183 (that is, the end opposite to the end that is coupled to the first part 182). The heat sink 77 may have any suitable structure and may comprise a plurality of conductive fins that extend radially outwards from the second part 183. Additionally or alternatively, the device may comprise a Peltier cooler 77 to increase the transfer of thermal energy from the second part 183. Furthermore, the device may additionally or alternatively comprise a thermal electric generator 77 to create electrical energy from the dissipation of thermal energy.

The second part 183 of the heat pipe 181 may advantageously enable thermal energy from the member 16 to be transferred to a relatively cool location that is not positioned along the longitudinal axis 27 of the first part 182 of the heat pipe 181. For example, where the object 12 is a gas turbine engine, the second part 183 of the heat pipe 181 may extend towards and into a bifurcation tube within the bypass duct of the gas turbine engine.

The object 12 includes a first wall 121 and a second wall 122 (which may be casing walls of a gas turbine engine for example). The first end 34 of the first part 182 of the heat pipe 181 extends through an opening 76 in the first wall 121 and the second end 36 of the first part 182 of the heat pipe 181 abuts an exterior surface of the second wall 122 around an opening 24 in the second wall 122.

The plug 68 is coupled to the second end 28 of the first tube 14. For example, the plug 68 may be coupled to the second end 28 via an adhesive. In another example, the plug 68 may be welded to the first tube 14. In a further example, the plug 68 may be integral with the first tube 14 and may define the second end 28 of the first tube 14.

The plug 68 may be sized and shaped to plug the opening 24 of the object 12 and thereby seal the cavity 22. For example, where the object 12 is a gas turbine engine and the opening 24 is a borescope port, the plug 68 may be sized and shaped to plug the borescope port and thereby seal the gas path within the gas turbine engine. In other examples, the plug 68 may be sized and shaped to plug the open second end 36 of the heat pipe 181 (for example, in an embodiment where the second end 36 of the heat pipe 181 protrudes through the opening 24 and into the cavity 22).

The connector arrangement 70 is configured to connect the apparatus 101 to the object 12. In some examples, the connector arrangement 70 comprises a plurality of fasteners 80 (such as screws or bolts) that extend through a ring 82 extending radially outwards from the first part 182 of the heat pipe 181 and into the first wall 121 of the object 12. In other examples, the connector arrangement 70 may include an alternative mechanism for connecting the apparatus 101 to the object 12 and may include an adhesive for example. Consequently, the heat pipe 181 may be fixed to the first wall 121 and be static relative to the first wall 121.

The connector arrangement 70 may be configured to enable an operator to connect the apparatus 101 to the object 12, and to enable the operator to disconnect and remove the apparatus 70 from the object 12. For example, where the connector arrangement 70 comprises a plurality of fasteners 80 as illustrated in FIG. 6, the operator may use a wrench to tighten the fasteners 80 to connect the apparatus 101 to the object 12. Similarly, the operator may use the wrench to loosen the plurality of fasteners 80 to disconnect the apparatus 101 from the object 12, and may then remove the apparatus 101 by hand, or by using a mechanical aid (such as a pulley system).

The plurality of optical fibres 71 have a first end positioned at the aperture 32 of the first tube 14 (and may be coupled to a lens within the aperture 32), and a second end connected to the optical sensor 74 and the light source 72. The optical sensor 74 and the light source 72 are positioned externally of the first tube 14 and consequently, the plurality of optical fibres 71 include a first part that extends along the length of the first tube 14 within the first cavity 30 between the aperture 32 and the first end 26 of the first tube 14, and a second part that extends from the first end 26 of the first tube 14 to the optical sensor 74 and the light source 72.

The light source 72 may be any suitable emitter of visible light and may comprise a light emitting diode or a laser. In some examples, the light source 72 may be configured to emit infrared radiation or ultraviolet radiation. While the light source 72 is illustrated as being positioned external to the first tube 14 in FIG. 6, it should be appreciated that in other examples, the light source 72 may be positioned within the first cavity 30 of the first tube 14 (at the aperture 32 for example).

The optical sensor 74 may be any suitable optical sensor and may be a charge coupled device (CCD) camera or a complementary metal oxide semiconductor (CMOS) camera for example. While the optical sensor 74 is illustrated as being positioned external to the first tube 14 in FIG. 6, it should be appreciated that in other examples, the optical sensor 74 may be positioned within the first cavity 30 of the first tube 14 (at the aperture 32 for example).

In operation, the light source 72 is configured to emit light which is conveyed to the aperture 32 of the first tube 14 via the plurality of optical fibres 71. At the aperture 32, the plurality of optical fibres 71 direct the light out of the aperture 32 and into the cavity 22 of the object 12. The light is then reflected by the surfaces of the object 12 and some of the reflected light is received at the aperture 32 which is conveyed to the optical sensor 74 via the plurality of optical fibres 71.

The actuator 20 is configured to move the first tube 14 between a first position in which the plug 68 seals the member 16 from the cavity 22 of the object 12, and a second position in which the member 16 is exposed to the cavity 22 of the object 12 (as illustrated in FIG. 6). The first position may be achieved by the plug 68 forming a seal with the opening 24, or by the plug 68 forming a seal with the second open end 36 of the heat pipe 181.

The apparatus 181 may provide several advantages. First, the plug 68 may provide an effective seal with the object 12 or with the heat pipe 181 and may consequently protect the member 16 from being damaged by fluids within the cavity 20 of the object 12. Second, the plug 68 may be sized and dimensioned to fit snugly inside the opening 24 of the object 12 and consequently, the object 12 may not require modification to be used with the apparatus 101. Third, the plug 68 may not comprise any movable mechanical parts and consequently, the plug 68 may be relatively simple and may be less likely to fail during operation. Fourth, the remote positioning of a sensor from the first tube 14 (such as the optical sensor 74 and the first tube 14 illustrated in FIG. 6) may provide more space for the sensor and thereby allow the sensor to have a larger sensor area with a higher resolution.

Figure 7:
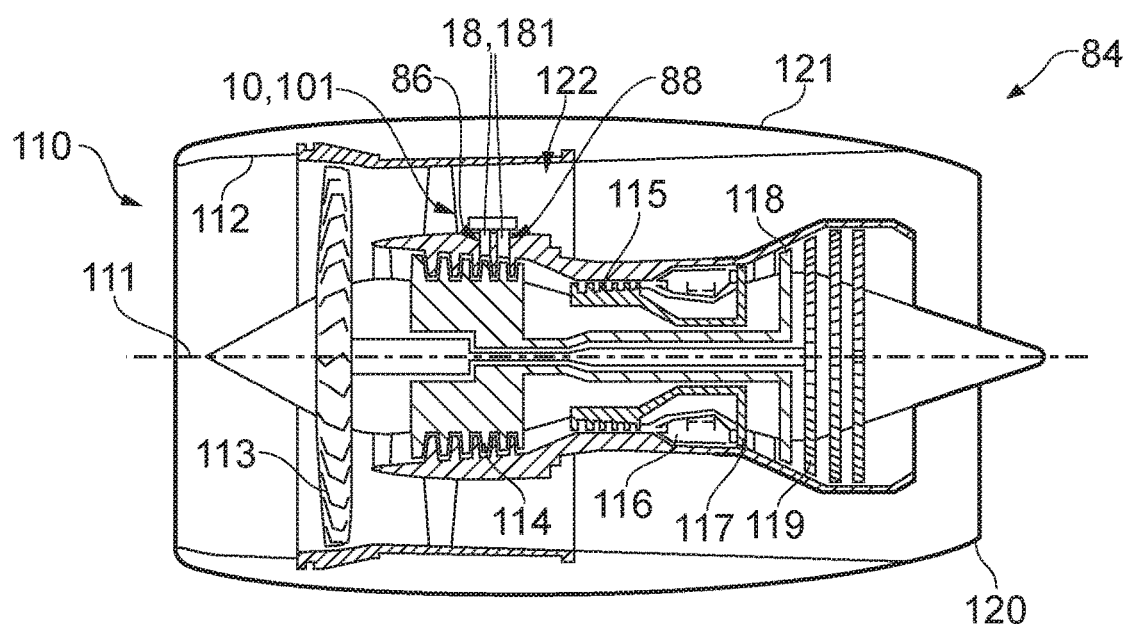
FIG. 7 illustrates a schematic cross sectional side view of a gas turbine engine and an apparatus for insertion into a cavity of an object according to various examples.

FIG. 7 illustrates a schematic cross sectional side view of a system 84 comprising a gas turbine engine 110 and apparatus 10, 101 as described in the preceding paragraphs.

The gas turbine engine 110 has a principal and rotational axis 111 and comprises, in axial flow series, an air intake 112, a propulsive fan 113, an intermediate pressure compressor 114, a high-pressure compressor 115, combustion equipment 116, a high-pressure turbine 117, an intermediate pressure turbine 118, a low-pressure turbine 119 and an exhaust nozzle 120. A nacelle 121 generally surrounds the engine 110 and defines both the intake 112 and the exhaust nozzle 120.

The gas turbine engine 110 operates so that air entering the intake 112 is accelerated by the fan 113 to produce two air flows: a first air flow into the intermediate pressure compressor 114 and a second air flow which passes through a bypass duct 122 to provide propulsive thrust. The intermediate pressure compressor 114 compresses the air flow directed into it before delivering that air to the high pressure compressor 115 where further compression takes place.

The compressed air exhausted from the high-pressure compressor 115 is directed into the combustion equipment 116 where it is mixed with fuel and the mixture combusted. The resultant hot combustion products then expand through, and thereby drive the high, intermediate and low-pressure turbines 117, 118, 119 before being exhausted through the nozzle 120 to provide additional propulsive thrust. The high 117, intermediate 118 and low 119 pressure turbines drive respectively the high pressure compressor 115, intermediate pressure compressor 114 and fan 113, each by a suitable interconnecting shaft.

Other gas turbine engines to which the present disclosure may be applied may have alternative configurations. By way of example such engines may have an alternative number of interconnecting shafts (two for example) and/or an alternative number of compressors and/or turbines. Furthermore, the gas turbine engine may comprise a gearbox provided in the drive train from a turbine to a compressor and/or fan.

The gas turbine engine 110 includes a first inspection port 86 and the apparatus 10, 101 extends inside the first inspection port 86. The second end 36 of the heat pipe 18, 181 extends into the gas path of the gas turbine engine 110 and the first end 34 of the heat pipe 18, 181 is positioned within the bypass duct 122 of the gas turbine engine 110.

In some examples, the gas turbine engine 110 may further comprise a second inspection port 88, and the system 84 may further comprise another apparatus 10, 101 that extends inside the second inspection port 88. The second end 36 of the heat pipe 18, 181 may extend into the gas path of the gas turbine engine 110 and the first end 34 of the heat pipe 18, 181 may be positioned within the bypass duct 122 of the gas turbine engine 110.

It will be understood that the invention is not limited to the embodiments above-described and various modifications and improvements can be made without departing from the concepts described herein. For example, an apparatus may comprise any one of, or any combination of, the plug 68, the connector arrangement 70, the one or more optical fibres 71, the light source 72, and the optical sensor 74.

In some examples, the heat pipe 18, 181 may include a single loop instead of the structure illustrated in FIG. 2. The single loop may include a relatively long, thin cavity that is looped from the first end 34 to the second end 36. In a first part of the loop there are pores or grooves without a vapour gap 44, and in a second part of the loop there is a hollow cavity without pores or grooves to allow the vapour to travel to the first end 34 for condensation. The heat pipe 18, 181 may include a plurality of such loops, or may include a single loop that spirals around. In the example of the heat pipe 181, the one or more loops may extend into the second part 183 where the fluid is condensed.

In various examples, the heat pipe 18, 181 may use a single phase approach (a liquid for example) rather than a two-phase evaporation and condensation approach. The liquid receives thermal energy at the second end 36 of the heat pipe 18, 181 and transfers thermal energy away at the first end 34 of the heat pipe 18 or in the second part 183 of the heat pipe 181.

Figure 8:
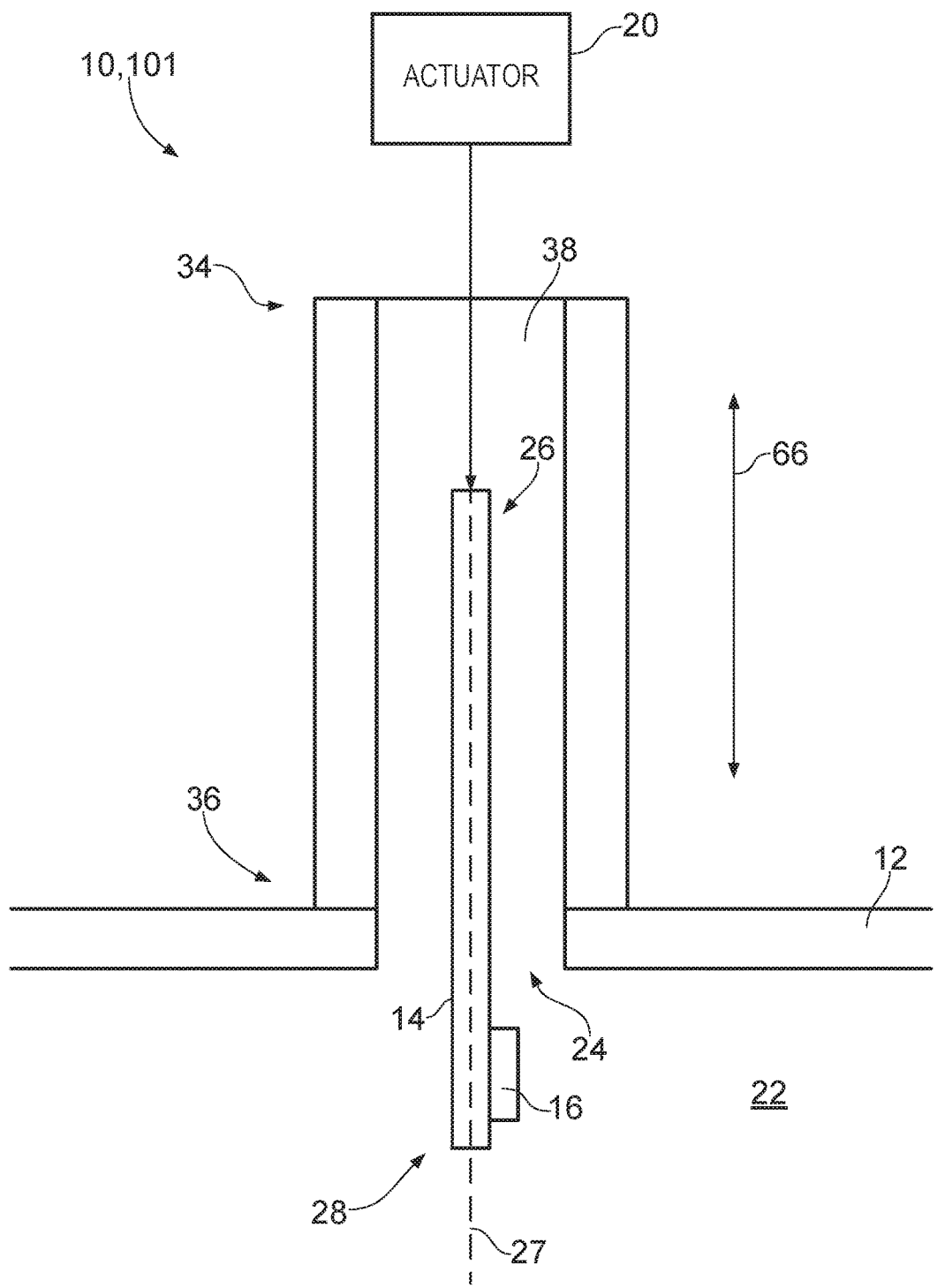
FIG. 8 illustrates a schematic cross sectional side view of apparatus for insertion into a cavity of an object according to various examples.

As illustrated in FIG. 8, the member 16 may be positioned on the exterior of the first tube 14 and the first tube 14 may not define the first cavity 30 (for example, the first tube 14 may be solid).

Except where mutually exclusive, any of the features may be employed separately or in combination with any other features and the disclosure extends to and includes all combinations and sub-combinations of one or more features described herein.

What is claimed is:

1. Apparatus for insertion into a cavity of an object, the apparatus comprising:
    a first tube comprising a first end, a second end and a first cavity extending between the first end and the second;
    a member positioned within the first cavity of the first tube and configured to enable an action to be performed;
    a heat pipe including a first end, a second end, and a second cavity extending between the first end and the second end, the first tube being positioned within the second cavity of the heat pipe; and
    an actuator configured to move the first tube relative to the heat pipe.

2. Apparatus as claimed in claim 1, wherein the heat pipe comprises a first part extending along a first longitudinal axis and including the second cavity, and a second part extending along a second longitudinal axis, the second longitudinal axis defining an angle with the first longitudinal axis.

3. Apparatus as claimed in claim 2, wherein the second longitudinal axis defines an angle of ninety degrees with the first longitudinal axis.

4. Apparatus as claimed in claim 1, wherein the heat pipe includes: an inner region for enabling fluid to flow to the second end of the heat pipe; an outer region for enabling fluid to flow to the second end of the heat pipe; and a channel for enabling vapour to flow to the first end of the heat pipe.

5. Apparatus as claimed in claim 4, wherein the inner region comprises a lattice structure defining a plurality of pores.

6. Apparatus as claimed in claim 4, wherein the outer region comprises a lattice structure defining a plurality of pores.

7. Apparatus as claimed in claim 5, wherein the plurality of pores have a median dimension in the range of five micrometres to two hundred and fifty micrometres.

8. Apparatus as claimed in claim 5, wherein the plurality of pores have a median dimension in the range of thirty micrometres to one hundred and twenty micrometres.

9. Apparatus as claimed in claim 4, wherein the inner region comprises a plurality of grooves and the outer region comprises a plurality of grooves.

10. Apparatus as claimed in claim 4, wherein the channel comprises a plurality of conduits that are interconnected at the first end of the heat pipe.

11. Apparatus as claimed in claim 1, further comprising a plug coupled to the second end of the first tube, the actuator being configured to move the first tube between a first position in which the plug seals the member from the cavity of the object, and a second position in which the member is exposed to the cavity of the object.

12. Apparatus as claimed in claim 1, further comprising a connector arrangement configured to connect the apparatus to the object.

13. Apparatus as claimed in claim 12, wherein the connector arrangement is configured to enable an operator to connect the apparatus to the object, and to enable the operator to disconnect and remove the apparatus from the object.

14. Apparatus as claimed in claim 1, wherein the member comprises one or more optical fibres, and the apparatus further comprises an optical sensor coupled to the one or more optical fibres, the optical sensor being positioned external to the first tube.

15. Apparatus as claimed in claim 1, wherein the member comprises an optical sensor, or wherein the member comprises repair apparatus for performing a repair on the object, or wherein the member comprises non-destructive examination (NDE) apparatus.

16. Apparatus as claimed in claim 1, wherein the object is a gas turbine engine, and wherein the cavity is a gas path of the gas turbine engine.

17. Apparatus for insertion into a cavity of an object, the apparatus comprising:
    a first tube comprising a first end and a second end;
    a member coupled to the first tube and configured to enable an action to be performed;
    a heat pipe including a first end, a second end, and a second cavity extending between the first end and the second end, the first tube being positioned within the second cavity of the heat pipe; and
    an actuator configured to move the first tube relative to the heat pipe.

18. A system comprising: a gas turbine engine including a first inspection port; and an apparatus as claimed in claim 1 extending inside the first inspection port.

19. A system as claimed in claim 18, wherein the gas turbine engine further comprises a second inspection port, and the system further comprises a second apparatus that is the same as the apparatus and extending inside the second inspection port.

20. A system as claimed in claim 18, wherein the first end of the heat pipe is positioned within a bypass duct of the gas turbine engine.

* * * * *